(12) United States Patent
Lechner

(10) Patent No.: US 9,603,537 B2
(45) Date of Patent: Mar. 28, 2017

(54) UNIT, ASSEMBLY, DEVICE AND METHOD FOR TESTING A SENSOR MEANS PROVIDED IN A MEDICAL LOCALISATION DEVICE

(75) Inventor: Timotheus Joan Marie Lechner, Drunen (NL)

(73) Assignee: APAD OCTROOI B.V., 's-Hertogenbos (NL)

( * ) Notice: Subject to any disclaimer, the term of this patent is extended or adjusted under 35 U.S.C. 154(b) by 266 days.

(21) Appl. No.: 13/260,984

(22) PCT Filed: Apr. 1, 2010

(86) PCT No.: PCT/NL2010/000061
§ 371 (c)(1),
(2), (4) Date: Jan. 12, 2012

(87) PCT Pub. No.: WO2010/114364
PCT Pub. Date: Oct. 7, 2010

(65) Prior Publication Data
US 2012/0101410 A1     Apr. 26, 2012

(30) Foreign Application Priority Data

Apr. 2, 2009   (NL) .................................. 2002708

(51) Int. Cl.
*A61B 5/00*   (2006.01)
*A61B 5/03*   (2006.01)
*A61B 17/34*   (2006.01)

(52) U.S. Cl.
CPC .......... *A61B 5/032* (2013.01); *A61B 17/3401* (2013.01); *A61B 2090/064* (2016.02)

(58) Field of Classification Search
CPC ...... A61B 5/4528; A61B 5/103; A61B 5/0053
USPC .................................................. 600/561, 587
See application file for complete search history.

(56) References Cited

U.S. PATENT DOCUMENTS

| 4,403,988 A | | 9/1983 | Binard et al. |
| 4,624,659 A | * | 11/1986 | Goldberg .......... A61M 25/1018 222/47 |
| 4,790,821 A | * | 12/1988 | Stines ........................ 604/97.03 |
| 4,801,293 A | | 1/1989 | Jackson |
| 5,810,770 A | | 9/1998 | Chin et al. |
| 6,120,457 A | * | 9/2000 | Coombes et al. ............ 600/486 |

(Continued)

FOREIGN PATENT DOCUMENTS

EP     0538259 A1     4/1993

*Primary Examiner* — Daniel Cerioni
(74) *Attorney, Agent, or Firm* — Hoffmann & Baron, LLP

(57) ABSTRACT

A unit, assembly and device suitable for a medical localization device suitable for localizing a region in a body with a distal hollow needle includes a tube extending from a proximal first end to a distal second end. The first end is designed to be in communication with a fluid filled container. The unit includes a first part of sensor means. The first part is a sensor interface, in which the sensor interface is provided to the tube between the first end and the second end. The sensor interface is suitable for observation of the pressure in a fluid in the tube that is in communication with the fluid in the container. The unit includes a closing device distally with respect to the sensor interface for varying the pressure in the fluid in the tube, in which the sensor interface is a membrane.

17 Claims, 4 Drawing Sheets

(56) References Cited

U.S. PATENT DOCUMENTS

| | | | |
|---|---|---|---|
| 2004/0215080 A1* | 10/2004 | Lechner ........................ | 600/463 |
| 2006/0247657 A1* | 11/2006 | Trieu ............................ | 606/102 |
| 2007/0038143 A1* | 2/2007 | Christensen et al. ......... | 600/561 |
| 2008/0103408 A1* | 5/2008 | Denton et al. ................ | 600/549 |
| 2010/0022918 A1* | 1/2010 | Fujie et al. ................... | 600/587 |
| 2010/0030102 A1* | 2/2010 | Poston et al. ................. | 600/561 |
| 2010/0179488 A1* | 7/2010 | Spiegel .............. | A61M 16/044 |
| | | | 604/240 |

* cited by examiner

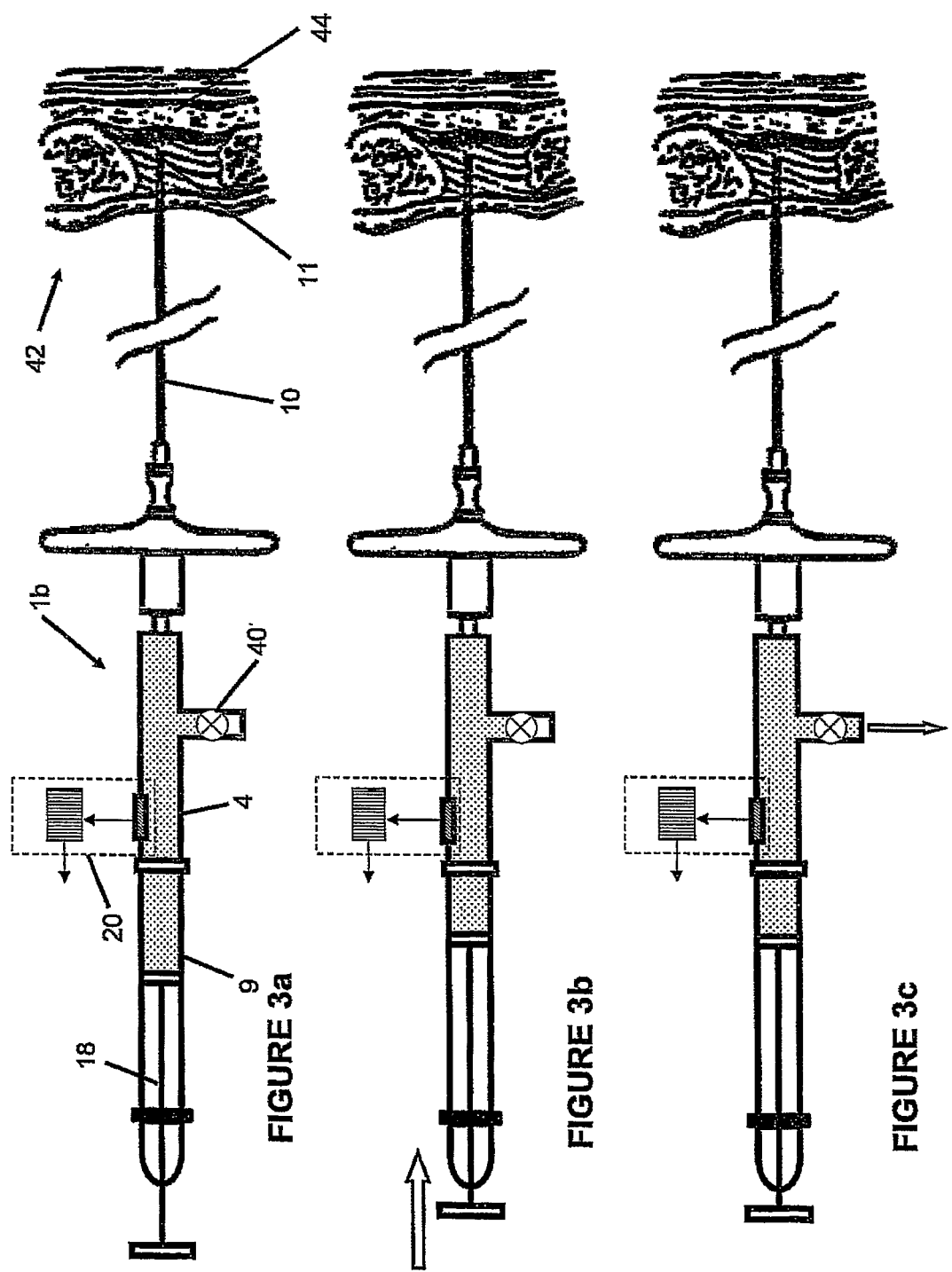

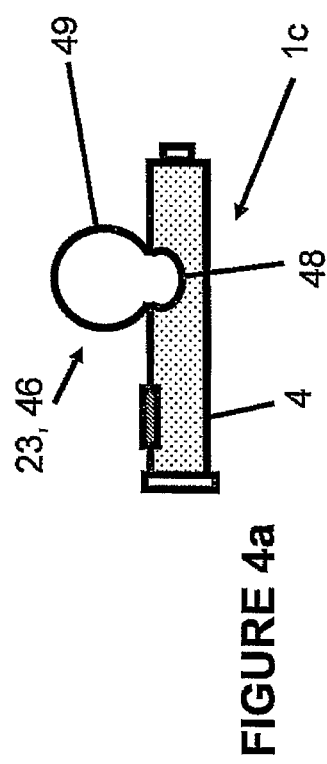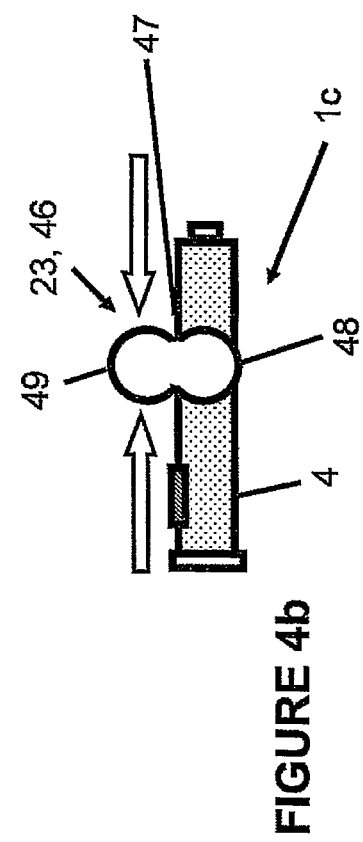

UNIT, ASSEMBLY, DEVICE AND METHOD FOR TESTING A SENSOR MEANS PROVIDED IN A MEDICAL LOCALISATION DEVICE

CROSS-REFERENCE TO RELATED APPLICATIONS

This application is the National Stage of International Application No. PCT/NL2010/000061, filed Apr. 1, 2010, which claims the benefit of Netherlands Application No. 2002708, filed Apr. 2, 2009, the contents of which is incorporated by reference herein.

FIELD OF THE INVENTION

The present invention relates to a unit, assembly, device and a method for testing a sensor means provided in a medical localisation device suitable for localizing a region in a body, such as an anatomical cavity with a distal hollow needle.

BACKGROUND OF THE INVENTION

Locating an anatomical cavity in a body, for example the body of a patient, is important, inter alia, for anaesthetics, in which it is often necessary for substances which have an anaesthetic action to be introduced into the anatomical cavity, such as for example the epidural cavity which is located in the vicinity of the spinal cord. To locate the anatomical cavity, it is generally known to use a medical localisation device such as a hollow needle and a reservoir filled with an isotonic liquid or with a gas mixture, and often an injection syringe with a displaceable plunger. When the point of the hollow needle reaches the anatomical cavity, the fluid flowing out of the needle is no longer subject to any resistance from surrounding tissue, and the pressure in the liquid drops. The person who is handling the assembly can feel this in the hand which he is using to operate the injection syringe. These pressure variations during handling of the assembly can also be fed back to the user by means of pressure information presented on a screen or by sound. For this purpose the assembly is provided with sensor means that measure the pressure variation of the liquid and generate a pressure-signal.

An example of an apparatus for locating anatomical cavities is disclosed inter alia in EP 0 538 259.

The known apparatus comprises a hollow needle, a fluid-filled reservoir which is in communication with the needle, pump means for pressurizing the fluid, measuring means for creating a pressure-measurement signal which is related to the pressure prevailing in the fluid, signal-conversion means for converting the pressure-measurement signal created by the measuring means into a form which is suitable for further processing, and reproduction means for emitting an acoustic signal which is related to the pressure-measurement signal which has been converted by the signal-conversion means.

The needle of the known apparatus is intended to be introduced into a body and is connected to the reservoir in the form of an injection syringe. The injection syringe contains fluid in the form of an isotonic liquid. The needle and the injection syringe are in communication with one another via a T-shaped connector. The pressure-measuring means, which are used to detect and measure the pressure prevailing in the liquid in the injection syringe, are also connected to this T-shaped connector and is in communication with the needle and injection syringe. The known apparatus also comprises a processor for processing a pressure-measurement signal created by the pressure-measuring means, in order that the rate of pressure variation can always be determined when in communication with the needle and the injection syringe, which pressure variation is primarily the consequence of the different tissue encountered when moving the needle in the body.

When the known apparatus is being used, the starting point is a situation in which the point of the needle is already situated in the vicinity of the cavity which is to be located. The needle, the injection syringe and the pressure-measuring means are set in communication to one another by changing the position of a switch in the T-shaped connector. In the injection syringe there is a plunger which functions as a pump means for displacing the liquid through the needle and thus produces pressure in the liquid. The pressure which is shown on the screen when there is no pressure being exerted on the plunger of the injection syringe is calibrated to zero. Then, the person who is handling the injection syringe and the needle brings the pressure in the liquid in the injection syringe to a defined level by exerting pressure on the plunger. During this process, he can read the level of the pressure from the screen at any time. When the liquid in the injection syringe has been brought to the required pressure, the person who is handling the device can move the needle towards the cavity in the body while using the pressure data displayed on the screen to carefully maintain a pressure on the plunger. When the level of the pressure variation exceeds a minimum level stored in the processor and/or the pressure variation rate over a defined time period is within minimum margins stored in the processor, the warning means are activated and emit a first, acoustic warning signal via acoustic reproduction means. If the pressure can be restored by slightly displacing the plunger, without further displacement of the needle, the first acoustic warning signal will stop. On the other hand, if a more abrupt pressure variation occurs and the pressure cannot be restored by displacing the plunger, the warning means emit a second acoustic warning signal, which clearly differs from the first warning signal. From the second warning signal, the person who is handling the device can infer that the point of the needle has reached the anatomical cavity and the he must stop moving the needle.

A drawback of the apparatus and method which are known from EP 0 538 259 is that it is unknown to the person who is handling the injection syringe if the measuring means and/or the signal-conversion means are working correctly. If the measuring means and/or the signal conversion means are defect, for example they give erroneous output or do not work at all, the instantaneous pressure data on the screen is shown wrongly. Moreover, emitted acoustic warning signals do not match with the actual pressure. It may also be possible that no warning signal is emitted at all even when the level of the pressure variation exceeds the minimum level stored in the processor and/or the pressure variation rate over a defined time period is within the minimum margins stored in the processor. This results in a handling of the syringe that can be dangerous. For example, the person who handles the syringe will pass the needle beyond the cavity and affect the spinal cavity or spinal cord which have particularly adverse results for the patient.

SUMMARY OF THE INVENTION

It is an object of the invention to at least partially eliminate at least one of the abovementioned drawbacks or to at least provide a usable alternative.

In particular, it is an object of the present invention to provide an improved unit for testing a sensor means provided in a medical localisation device in which the above drawback is eliminated or at least reduced.

According to the present invention, the above object is achieved by providing a unit according to the present invention. The unit is suitable for a medical localisation device. The medical localisation device is suitable for localizing a region in a body with a distal hollow needle. The unit comprises a tube extending from a proximal first end to a distal second end. The first end is designed to be in communication with a fluid filled container. The unit further comprises at least a first part of sensor means. This first part is a sensor interface, in which the sensor interface is provided to the tube between the first end and the second end. The sensor interface is suitable for observation of the pressure in a fluid in the tube. The fluid in the tube is in communication with the fluid in the container. Furthermore, the unit comprises a closing device distally with respect to the sensor interface for varying the pressure in the fluid in the tube, in which the sensor interface is a membrane.

Having a closing device according to the present invention allows the pressure in the tube to be varied in a controlled and known manner. The person who handles the closing device thereby is able to control the pressure in the tube. Having this control allows him to test the medical localisation device as the actual pressure and/or pressure variation in the tube is controllable and known. Testing comprises the comparison between the known actual pressure and/or pressure variation and the output of the sensor means. The results of the comparison is representative for the operation of the sensor means. The region in the body can for example be an anatomical cavity. The fact that the sensor interface is a membrane allows an easy to manufacture structure of the tube. The membrane is located nearby or on an outer wall of the tube instead of substantially inside the tube. Therefore, there is no need for a more complicated construction that holds a sensor interface in place inside the tube and/or transferring the output of the sensor interface outside the tube. Moreover, the membrane has an extra function besides providing an observation of the pressure. As the membrane is located nearby or on the outer wall it is replacing the outer wall at that location. This extra function is keeping fluid inside the tube. This orientation of the membrane allows the side of the membrane facing outwards (towards for example an ambient) to be accessed easily from outside and thus allows an easy interface with the output of the sensor interface.

In a preferred embodiment of the unit according to the invention the closing device is provided with an at least partially flexible balloon that is in open communication with the tube, in which the balloon closes the tube on pressure when the balloon is compressed.

The fact that an at least partially flexible balloon is used to close the tube on pressure makes it easy for the user of the medical localisation device to close the tube on pressure. The balloon can be compressed single handed as only compressing the balloon is needed. The other hand can still be used to hold the medical localisation device in place.

In a further preferred embodiment of the unit according to the invention the tube is divided in a first tube portion and a second tube portion, in which the balloon provides a communication between the first tube portion and the second tube portion.

The fact that the balloon communicates in between the first tube portion and the second tube portion results in an easy to manufacture tube. Moreover, it allows the balloon to be symmetrical around the longitudinal axis of the tube portions. Therefore there is no need to rotate the unit along its longitudinal axis in order for a hand to reach the balloon and successively compress the balloon.

In an alternative preferred embodiment of the unit according to the invention an opening is provided in the outer wall of the tube through which the balloon extends, such that the balloon defines an inner part and an outer part, in which the inner part closes the tube on pressure when the outer part is compressed.

The fact that the inner part closes the tube on pressure when the outer part is compressed allows the tube to be formed in one part having only a relatively small opening in order for the balloon to fit in. Moreover, it allows a more regulated closing of the tube. The inner part of the balloon closes the tube due to an expansion of the inner part. This expansion can be regulated accurately by compressing the outer part of the balloon by hand. The relation between the amount and form of expansion of the inner part of the balloon and the compression of the outer part of the balloon can be predefined by choosing a dedicated shape, orientation and material of the balloon.

In a preferred embodiment of the unit according to the invention the unit comprises first coupling means at the first end, that provide a releasable communication between the fluid filled container and the first end of the tube.

This has as advantage that the unit is disposable with respect to the fluid filled container or the fluid filled container is disposable with respect to the unit. This reduces costs and/or is convenient from a contamination point of view. It also allows a communication with different types of fluid filled containers. For example the fluid filled container can be of different brand, size or interface type and can include a pressure means that is automatic or manual.

In a preferred embodiment of the unit according to the invention the unit comprises second coupling means at the second end, that provide a releasable communication between the hollow needle and the second end of the tube.

This has as advantage that the unit is disposable with respect to the hollow needle or the hollow needle is disposable with respect to the unit. This reduces costs and/or is convenient from a contamination point of view. It allows a communication with different types of hollow needles. For example a hollow needle can be of different brand, size or interface type. A hollow needle can also contain a handle for better grip.

The object of the present invention is also achieved by an assembly according to the present invention, comprising a unit according to the invention and the hollow needle that is in communication with the second end of the tube.

In a preferred embodiment of the assembly according to the invention the assembly has the closing device provided to the tube.

This has as advantage that the tube is provided with the at least one part of the sensor interface and the closing device which result in compatibility with more types of hollow needles. This has as advantage that the unit is disposable with respect to more types of hollow needles or more types of hollow needles are disposable with respect to the unit.

The object of the present invention is also achieved by a medical localisation device according to the present invention, comprising a unit according to the invention, a fluid filled container that is in releasable communication with the first end of the tube and at least a second part of the sensor means, the second part being a generator for generation of an electric pressure signal that is representative of an observation from the sensor interface.

It is a further object of the present invention to provide a method for testing a sensor means in which the drawback of not knowing whether the measuring means and/or the signal-conversion means are working correctly is eliminated or at least reduced. This drawback concerns the person who is handling the injection syringe. The sensor means are provided in a medical localisation device. The medical localisation device is designed for localizing a region in a body with a distal hollow needle.

The above object is achieved by providing a method according to the present invention. This relates to a method for testing a sensor means provided in a medical localisation device suitable for localizing a region in a body with a distal hollow needle, in which prior to the method the medical localisation device comprises a closing device in a first state of the closing device. The method comprises the step of introducing a fluid into the medical localisation device and the step of determining the pressure in the fluid using the sensor means, in which the sensor means generates a pressure signal which is representative of the pressure in the fluid. The method furthermore comprises the step of applying an elevated pressure to the fluid and the step of operating the closing device to a second state of the closing device, such that the pressure in the fluid varies. Furthermore, the method comprises the step of making a first observation of the pressure signal prior to a variation resulting from the operation of the closing device or the appliance of an elevated pressure to the fluid and the step of making a second observation of the pressure signal after a variation of the pressure in the fluid resulting from the operation of the closing device or the appliance of an elevated pressure to the fluid. The method furthermore comprises the step of comparing the first observation with the second observation, in which the comparison is representative to the operation of the sensor means.

Following the steps of the method of the present invention allows the pressure in the tube to be varied in a controlled and known manner. The person who handles the closing device thereby is able to control the pressure in the tube for example by operating the closing device or applying an elevated pressure. Before one of these steps a first observation is made by the sensor means. After one of these steps a second observation is made by the sensor means. Having this control allows him to test the medical localisation device as the actual pressure and/or pressure variation in the tube is controllable and known. Testing comprises the comparison between the first observation and the second observation. The results of the comparison is representative to the operation of the sensor means.

In a preferred embodiment of the method according to the invention the second state of the closing device is setting a communication between the fluid and an ambient pressure, such that the pressure in the fluid decreases.

This allows a sequence of steps (among other possible sequences) wherein the initial first state of the closing device is closed, such that the fluid can stream through the localisation device, but not through the closing device to ambient space. Firstly, an elevated pressure is applied to the fluid. Secondly, a first observation of the pressure signal is made. Thirdly, the closing device is operated to the second state (ambient). Fourthly, a second observation is made. The pressure in the fluid should decrease due to the continuing appliance of the elevated pressure and the fluid being in communication with ambient space. Lastly, the first observation is compared with the second observation and is representative to the operation of the sensor means.

In a preferred embodiment of the method according to the invention the second state of the closing device is closing the medical localisation device from pressure, such that the pressure in the fluid increases.

This allows a sequence of steps (among other possible sequences) wherein the initial first state of the closing device is an open position, such that fluid can stream through the localisation device. Firstly, an elevated pressure is applied to the fluid. Secondly, a first observation of the pressure signal is made. Thirdly, the closing device is operated to the second state (closed). The pressure in the fluid increases due to the continuing appliance of the elevated pressure and a closed medical localisation device. Fourthly, a second observation is made. Lastly, the first observation is compared with the second observation and is representative to the operation of the sensor means.

In a preferred embodiment of the method according to the invention the medical localisation device is provided with a tube and with a fluid filled container and the method comprises the step of coupling a proximal first end of the tube with the fluid filled container using first coupling means, in which the first coupling means provide a releasable communication between the container and the first end of the tube.

The step of coupling the first end of the tube with the fluid filled container allows a method that can be applied to different kinds of fluid filled containers. This allows for flexibility when performing the method. For example fluid filled containers of different brands or different sizes, shapes or other characteristics can be used. Moreover, it allows the tube to be disposable. The tube can be provided with sensor means and the closing device.

In a preferred embodiment of the method according to the invention the medical localisation device is provided with a tube and with the hollow needle and comprises the step of coupling a distal second end of the tube with the hollow needle using second coupling means, in which the second coupling means provide a releasable communication between the hollow needle an the second end of the tube.

The step of coupling the second end of the tube with the hollow needle allows a method that can be applied to different kinds of hollow needles. This allows for flexibility when performing the method. For example, hollow needles of different brands or different sizes, shapes, thickness or other characteristics can be used. Moreover, it allows the tube and/or needle to be disposable. The tube can be provided with sensor means and the closing device.

In a further embodiment of the method according to the invention a hollow needle is at least partly inside the body, such as a human body.

The fact that the hollow needle is inside a human body allows testing of the medical localisation device during invasion. This gives more confidence and safety to the user of the medical localisation device.

In an embodiment of the method according to the invention the medical localisation device is entirely outside a human body.

The fact that the medical localisation device is entirely outside a human body allows testing before and/or after invasion into a human body. When the method is performed before invasion it increases confidence for the user and safety in general as the sensor means are tested on their performance before use. When the method is performed after invasion it ascertains the correct feedback of a monitoring of the invasion. During invasion the observations made by the sensor means can be monitored and registered and used for analysis. This analysis can be relevant if additional complications occur and when one wants to know what the origin of such a complication was. The said observations in such a case are helpful.

These and further embodiments of the unit and the method according to the invention are described herein.

BRIEF DESCRIPTION OF THE DRAWINGS

These and other aspects, characteristics and advantages of the present invention will be explained in more detail by means of the following description of two preferred embodiments of a unit according to the invention and two preferred embodiments of a method according to the invention with reference to the drawings, in which identical reference numerals denote identical components, and in which:

FIGS. 2a, 2b and 2c seen consecutively show one possible sequence of steps of a first preferred embodiment of the method of the invention. Wherein FIG. 2a shows a side view of the first preferred embodiment of the unit of FIG. 1. These sequence of steps are performed outside a human body.

FIGS. 3a, 3b and 3c seen consecutively show one possible sequence of steps of a second preferred embodiment of the method of the invention. These sequence of steps are performed inside a human body. Wherein FIG. 3a shows a side view of a second preferred embodiment of the unit.

FIGS. 4a, and 4b seen show an alternative embodiment of the unit.

DETAILED DESCRIPTION OF THE INVENTION

Figure 1:
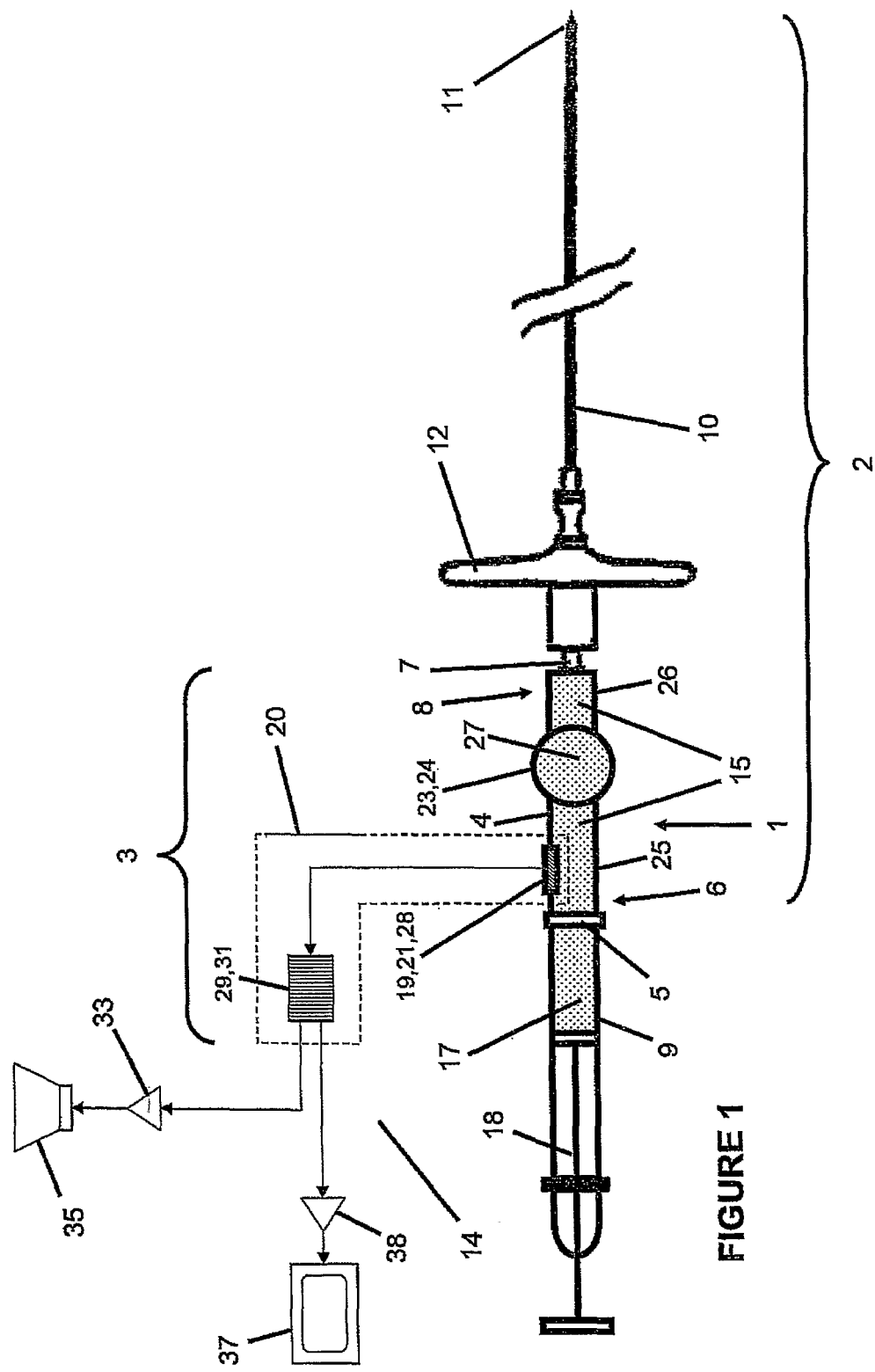
FIG. 1 shows a side view of a first preferred embodiment of a unit according to the invention.

FIG. 1 shows a unit 1 according to the invention. FIG. 1 also shows a system 2, comprising the unit 1 and a hollow needle 10. Also a medical localisation device 3 is shown, comprising the unit 1, a fluid filled container 9 and a generator 29.

The unit 1 comprises a tube 4 and has first coupling means 5 on a proximal first end 6 and second coupling means 7 on a distal second end 8. Proximal means close to the person who is handling the unit. Distal means away from the person who is handling the unit. The first coupling means 5 provide a releasable communication between a fluid filled container 9 and the first end 6. The second coupling means 7 provide a releasable communication between a hollow needle 10 with a needle point 11 and the second end. Therefore, the second coupling means 7 allow a communication between the hollow needle 10 and the tube 4. The hollow needle 10 is provided with a handle 12, which can be held by the person who is handling the hollow needle 10, for example a physician. The tube 4 comprises a fluid filled space 15.

The fluid filled container 9 is in the form of an injection syringe and is positioned in line with the hollow needle 10. The fluid filled container 9 comprises a fluid-filled space 17 that is in communication with the fluid filled space 15 of the tube and a displaceable plunger 18 which closes off the said container 9 in a sealed manner on one side.

The unit 1 is provided with at least a first part 19 of sensor means 20, the first part being a sensor interface 21 located between the first end 6 and the second end 8. The sensor interface 21 is suitable for observation of the pressure in the fluid filled space 15 of the tube. A closing device 23 is placed distally with respect to the sensor interface 21. Here, the tube 4 comprises the closing device 23 between the second end 8 and the sensor interface 21. This closing device 23 is in the form of a flexible balloon 24 that is in open communication with both ends 6,8 of the tube 2. This flexible balloon 24 divides the tube 4 in a first tube portion 25 and a second tube portion 26. The balloon 24 provides a communication between the first tube portion 25 and the second tube portion 26. When the balloon 24 is pressed, for example using a thumb and an index finger, the balloon 24 closes the tube 4 on pressure at that location such that it at least narrows the communication such that a pressure variation can occur. The balloon 24 comprises a fluid filled space 27 that is in communication with the fluid filled space 15 of the tube.

The displaceable plunger 18 in this case functions as a pump means for generating pressure in the fluid filled spaces 15,17,27 of the tube, container and balloon. The container 9 is in communication with the hollow needle 10 via the tube 4, the balloon 24 and the coupling means 5,7, it being possible for fluid to flow out of the container 9 into the hollow needle 10. The fluid in the container 9 may be a gas or a liquid, for example a sterile, isotonic liquid.

To observe the pressure in the fluid the sensor interface 21 is provided with a membrane 28. An output of the membrane 28 is connected to an input of a generator 29 that generates electric pressure signals. This generator is a second part 31 of the sensor means 20. The generator 29 is able to convert an observation provided by the membrane 28 into the electric pressure signal which can be used for further processing. The electric pressure signal can be for example an electric voltage. This electric voltage can be used as input for an synthesizer 33 that generates sounds through a loudspeaker 35 that is representative to the observed pressure. An alternative to the synthesizer is displaying the electric voltage on a screen 37 after it has been amplified by an amplifier 38. In FIG. 1 the membrane 28 and the generator 29 are separate elements, making the unit 1 disposable at lower recurrent price as the generator 29 is not part of the unit 1.

Figure 2A:
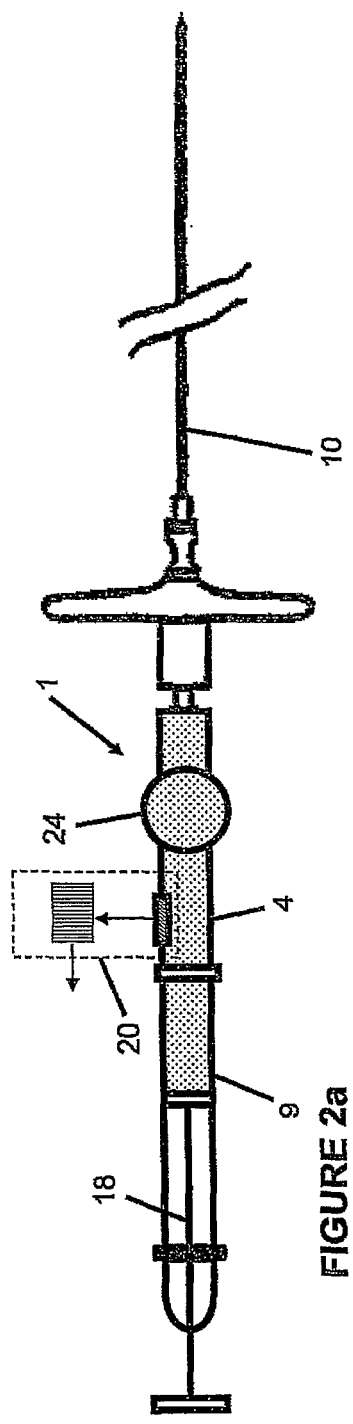
Figure 2B:
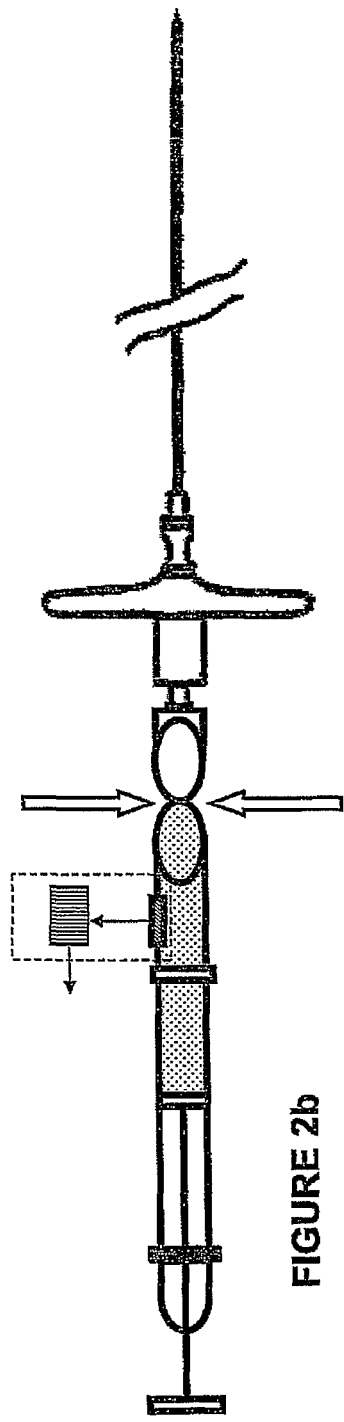
Figure 2C:
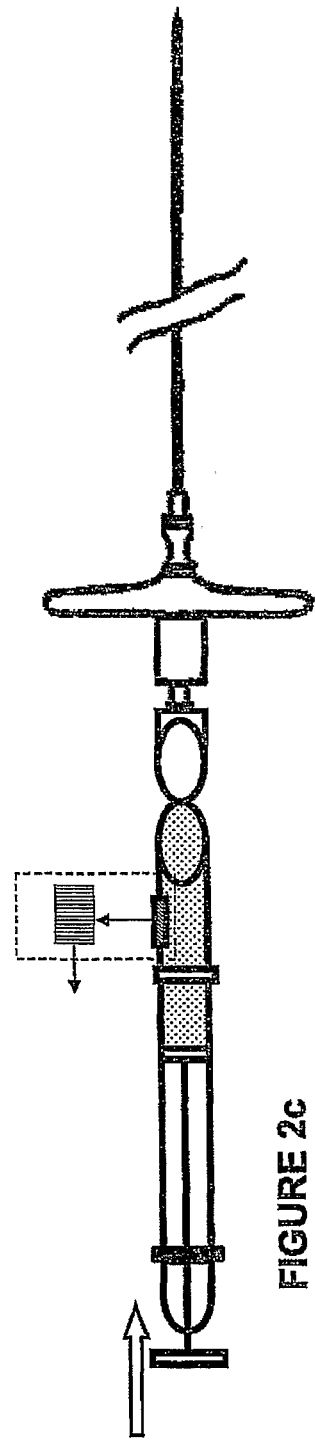

FIGS. 2a, 2b and 2c show a sequence of the use of the first preferred embodiment of unit 1 shown in FIG. 1.

The sensor means 20 can be tested by performing the steps of a first preferred embodiment of the method according to the invention. The unit 1 is entirely outside a human body, before the needle 10 enters the human body, as shown in FIG. 2a and the balloon 24 is in an open position. Firstly, an elevated pressure in the fluid is applied by moving the plunger 18 (not shown in the figures). The pressure will built up in the fluid and as a result of this pressure, the fluid will tend to flow out via the needle point 11. The sensor means 20 shall provide a pressure signal according to the actual pressure in the tube 4. This pressure is observed in a first observation of the user. Secondly, as is shown in FIG. 2b by means of arrows, the balloon 24 is pressed such that it closes the tube 4. This results in an increase of the pressure in the fluid between the balloon 24 and the plunger 18. When the plunger 18 is continued to be applied, which is shown in FIG. 2c by means of an arrow, the pressure shall continue to increase. The increased pressure is observed in a second observation of the user. Thirdly, the first observation and the second observation are compared by the user and is representative for the operation of the sensor means 20. As the user knows that closing the tube 4 on pressure results in an increase of pressure between the plunger 18 and the balloon 24, he expects to have this feedback from the sensor means 20. If the expected feedback is not observed this is an indication that the sensor means 20 are not functioning correctly.

FIGS. 3a, 3b and 3c show a unit 1b in a second preferred embodiment of the invention. The unit 1b is largely equal to the unit 1 as shown in FIG. 1. Similar components are denoted with the same numerals as in FIG. 1, except for the closing device 23 that is not provided with a balloon 24, but with a switch, such as a valve 40. FIGS. 3a, 3b and 3c seen consecutively show one possible sequence of steps of a second preferred embodiment of the method of the invention. In FIG. 3a the unit 1b of the second preferred embodiment shows specifically its use for locating an anatomical cavity 44, in particular the epidural cavity, in a human body. A small section of a human body is illustrated in cross section in FIG. 3a and is denoted by reference numeral 42. The anatomical cavity or epidural cavity is denoted by reference numeral 44. The needle point 11 is situated in the vicinity of the epidural cavity 44.

In this second preferred embodiment the closing device 23 is in the form of a switch or valve 40. The valve 40 has two states. In one state the valve 40 is closed and no communication via the valve 40 is made between the tube 4 and ambient pressure. When in the other state the valve 40 is open and there is a communication via the valve 40 between the tube 4 and ambient pressure.

The sensor means 20 can be tested. Firstly, an elevated pressure in the fluid is applied by moving the plunger 18 as shown in FIG. 3b. The pressure will be built up in the fluid and as a result of this pressure, the fluid will tend to flow out via the needle point 11. The valve 40 is closed. Depending on where the needle point 11 is situated a certain resistance is expressed as pressure which has to be overcome by the person who is exerting a force on the plunger 9. For example, the needle point 11 can be located outside or inside a body tissue. The sensor means 20 shall provide a pressure signal accordingly. This pressure is observed in a first observation of the user. Secondly, as is shown in FIG. 3c, the valve 40 is set to open and the tube 4 is communication with ambient pressure. This results in a decrease of the pressure in the fluid between the valve 40 and the plunger 18. The decreased pressure is observed in a second observation of the user. Thirdly, the first observation and the second observation are compared by the user and is representative for the operation of the sensor means 20. As the user knows that opening the valve 40 results in a decrease of pressure between the plunger 18 and the valve 40, he expects to have this feedback from the sensor means 20. If the expected feedback is not observed this is an indication that the sensor means 20 are not functioning correctly.

FIGS. 4a and 4b show an alternative embodiment of a unit 1c. The unit 1c is largely equal to the unit 1 as shown in FIG. 1. Similar components are denoted with the same numerals as in FIG. 1, except for the closing device 23 that is now provided with a balloon 46 that extends through the outer wall 47 of the tube 4. The balloon 46 defines an inner part 48 and an outer part 49. When the outer part 49 is compressed, as shown in FIG. 4b, the inner part 48 closes or at least narrows the tube 4, such that a pressure variation can occur. Arrows in FIG. 4b, show the compression of the outer part 49. For example, the compression results by applying a force in line with the arrows using an index finger and a thumb.

The invention is not limited to the described embodiments.

Alternatively, the closing device 23 does not closes the tube 4 entirely but closes the tube 4 at least partly or narrows the tube 4, such that a pressure variation still occurs.

As an alternative to using a plunger 18 as the pump means, it is also possible, for example, to use bellows or mechanical operated pumping means, such as electric pump means.

An alternative to a membrane 28 is an electrical pressure gauge.

Alternatively, the membrane 28 and the generator 29 form a single unit instead of two separate elements.

Alternatively, the tube is made of any suitable material and is made from a material that is stiff or is made from a material that is flexible.

In an alternative, the tube is made of multiple parts.

In another alternative, the tube has different types of shape, for example bended with a sharp edge or a smooth edge. In an example, the tube is T-shaped.

In an alternative, the unit comprises third part of sensor means. In an example the first part of sensor means, the first part being a sensor interface, is in communication with a second part of the sensor means, the second part being a generator, through a third part of sensor means, the third part being a hose or another tube. In this alternative the first part of sensor means can be located on a distance from the second part of sensor means.

In an alternative to the first preferred embodiment of the method, the balloon 24 is pressed before the plunger 18 is applied. The first observation is made before the plunger 18 is applied and the second observation is made after or during the appliance of the plunger 18. The last step is the comparison between the first observation and the second observation.

In an alternative, the closing device is a valve.

In an alternative, the closing device is provided integrally to the tube at a location distal from the sensor means where the tube is designed to be weakened or softened. For example, the tube is made of a flexible material which is weak or soft and can be pressed together such that it closes off the tube distally from the sensor means.

In an alternative to the first preferred embodiment of the method, the steps are performed with the hollow needle 10 at least partly inside a body, such as a human body.

In an alternative to the first preferred embodiment of the method, the steps are performed without the unit 1,1b being connected to the hollow needle 10.

Alternatively, the first- and second coupling means 5,7 can be standardized couplings or dedicated couplings. Standardized couplings provide a coupling of for example Luer needles and/or containers with the unit 1, 1b. Other standards are possible too.

In an alternative, the sensor means 20 comprises the synthesizer 33, the loudspeaker 35, the amplifier 38 and the screen 37.

A unit according to the invention is foreseen, wherein the first end of the tube communicates integrally with the fluid filled container.

This has as advantage that the unit and fluid filled container form a whole and are integrated which has as advantage that there is no need to connect the fluid filled container to or release the fluid filled container from the unit. This saves time and reduces possible errors, such as connecting the wrong fluid filled container to the unit.

Also a unit according the invention is foreseen, wherein the second end communicates integrally with the hollow needle.

This has as advantage that the unit and the hollow needle form a whole and are integrated which has as advantage that there is no need to connect the hollow needle to or release the hollow needle from the unit. This saves time and reduces possible errors, such as connecting the wrong hollow needle to the unit.

An assembly according to the invention is foreseen, wherein the closing device is provided to the hollow needle.

This has as advantage that this location of the closing device is preferable in terms of easy handling. For example, when the assembly is operated using a right hand it may be convenient for the user that the closing device is distal from the right hand. In case a handle is located between hollow needle and tube this means that it is convenient that the closing device is provided to the hollow needle.

The invention claimed is:

1. A unit suitable for a medical localisation device, wherein the unit is suitable for localizing a region in a body with a distal hollow needle connected to the unit, wherein the needle is configured to enter the body at least partially, comprising:
   a tube having an outer wall extending from a proximal first end of the tube to a distal second end of the tube, wherein the proximal first end is designed to be in communication with a fluid filled container;
   at least a first part of sensor means, the first part being a sensor interface, wherein the sensor interface is provided to the tube between the proximal first end and the distal second end, wherein the sensor interface is suitable for observation of the pressure in a fluid in the tube, wherein the sensor interface is a membrane that is configured to remain outside the body, wherein the membrane permanently forms and/or replaces a part of the outer wall of the tube and wherein the membrane is configured to keep fluid inside the tube during observation of the pressure to prevent an outer wall of the membrane from coming into contact with the fluid; and
   a closing device arranged distally with respect to the sensor interface, wherein the closing device is configured to vary the pressure in the fluid in the tube by closing at least partially the tube.

2. The unit according to claim 1, wherein the closing device is provided with an at least partially flexible balloon that is in open communication with the tube, and wherein the balloon closes the tube on pressure when the balloon is compressed.

3. The unit according to claim 2, wherein the tube is divided in a first tube portion and a second tube portion, and wherein the balloon provides a communication between the first tube portion and the second tube portion.

4. The unit according to claim 2, wherein an opening is provided in the outer wall of the tube through which the balloon extends, such that the balloon defines an inner part and an outer part, and wherein the inner part closes the tube on pressure when the outer part is compressed.

5. The unit according to claim 1, further comprising first coupling means at the proximal first end, that provide a releasable communication between the fluid filled container and the proximal first end of the tube.

6. The unit according to claim 1, further comprising second coupling means at the distal second end, that provide a releasable communication between the hollow needle and the distal second end of the tube.

7. An assembly, comprising:
   a unit according to claim 1; and
   the hollow needle that is in releasable communication with the second end of the tube.

8. The assembly according to claim 7, wherein the closing device is provided to the tube.

9. A medical localisation device, comprising:
   a unit according to claim 1;
   the fluid filled container that is in releasable communication with the first end of the tube; and
   at least a second part of the sensor means, the second part being a generator for generation of an electric pressure signal that is representative of an observation from the sensor interface.

10. A method for testing a sensor means provided in a medical localisation device suitable for localizing a region in a body with a distal hollow needle, wherein the medical localisation device comprises a closing device, wherein, prior to the method, the closing device is in a first state of the closing device, wherein the method comprises the steps:
    providing a unit suitable for a medical localisation device according to claim 1;
    introducing a fluid into the medical localisation device;
    determining the pressure in the fluid using the sensor means, wherein the sensor means generates a pressure signal which is representative of the pressure in the fluid;
    applying an elevated pressure to the fluid;
    operating the closing device to a second state of the closing device, such that the pressure in the fluid varies;
    making a first observation of the pressure signal prior to a variation resulting from the operation of the closing device or the appliance of an elevated pressure to the fluid by closing at least partially the tube;
    making a second observation of the pressure signal after a variation of the pressure in the fluid resulting from the operation of the closing device or the appliance of an elevated pressure to the fluid; and
    comparing the first observation with the second observation, wherein the comparison is representative to the operation of the sensor means.

11. The method according to claim 10, wherein a pumping means is provided in the medical localisation device for the appliance of an elevated pressure to the fluid.

12. The method according to claim 10, wherein the second state of the closing device is setting a communication between the fluid and an ambient pressure, such that the pressure in the fluid decreases.

13. The method according to claim 10, wherein the second state of the closing device is closing the medical localisation device from pressure, such that the pressure in the fluid increases.

14. The method according to claim 10, wherein the medical localisation device is provided with a tube and with a fluid filled container and the method comprises the step of:
    coupling a proximal first end of the tube with the fluid filled container using first coupling means, wherein the first coupling means provide a releasable communication between the container and the proximal first end of the tube.

15. The method according to claim 10, wherein the medical localisation device is provided with a tube and with the distal hollow needle and wherein the method comprises the step of:
    coupling a distal second end of the tube with the hollow needle using second coupling means, wherein the second coupling means provide a releasable communication between the hollow needle and the distal second end of the tube.

16. The method according to claim 14, wherein the hollow needle is at least partly inside the body, such as a human body.

17. The method according to claim 10, wherein the medical localisation device is entirely outside a human body.

* * * * *